United States Patent [19]

Kuma

[11] Patent Number: 4,929,756

[45] Date of Patent: May 29, 1990

[54] PROCESS FOR PREPARING OXIMES

[75] Inventor: Kiyoji Kuma, Kitakyushu, Japan

[73] Assignee: Mitsubishi Kasei Corporation, Tokyo, Japan

[21] Appl. No.: 360,034

[22] Filed: Jun. 1, 1989

[30] Foreign Application Priority Data

Jun. 13, 1988 [JP] Japan ................................ 63-145033

[51] Int. Cl.$^5$ ............................................. C07C 131/04
[52] U.S. Cl. ..................................... 564/267; 564/253; 564/268; 564/265; 564/266
[58] Field of Search ................. 564/253, 267, 265, 268

[56] References Cited

U.S. PATENT DOCUMENTS

| | | | |
|---|---|---|---|
| 2,749,358 | 6/1956 | Reilly | 564/267 |
| 3,215,730 | 11/1965 | Spathe et al. | 564/267 |
| 3,344,187 | 9/1967 | Caprara et al. | 564/267 |

FOREIGN PATENT DOCUMENTS

| | | | |
|---|---|---|---|
| 230864 | 12/1963 | Austria | 564/267 |
| 1941428 | 3/1971 | Fed. Rep. of Germany | 564/267 |
| 2547836 | 4/1976 | Fed. Rep. of Germany | 564/267 |
| 2508247 | 7/1980 | Fed. Rep. of Germany | 564/267 |

OTHER PUBLICATIONS

Kondo et al., Chem. Abst., vol. 86, #29433e, (1977).
Kondo et al., Chem. Abst., vol. 86, #43284p, (1977).
Patent Abstracts of Japan, unexamined applications, C field, vol. 1, No. 64, Jun. 22, 1977, p. 969.
Patent Abstracts of Japan, unexamined applications, C field, vol. 2, No. 34, Mar. 8, 1978, p. 4381.

*Primary Examiner*—James H. Reamer
*Attorney, Agent, or Firm*—Oblon, Spivak, McClelland, Maier & Neustadt

[57] ABSTRACT

A process for preparing an oxime, which comprises reacting a ketone or an aldehyde with nitrogen monoxide and hydrogen in the presence of a platinum group metal catalyst to form the corresponding oxime.

12 Claims, No Drawings

PROCESS FOR PREPARING OXIMES

The present invention relates to a process for producing oximes. Particularly, the present invention relates to a process for producing oximes directly from the corresponding ketones or aldehydes.

For example, cyclohexanone oxime is industrially useful as an intermediate for producing caprolactam as a starting material for nylon. It is usually prepared by reacting cyclohexanone synthesized by various methods, with hydroxylamine.

However, in such a method, it is necessary to use hydroxylamine in the form of an inorganic salt such as a sulfate or hydrochloride for the stability of hydroxylamine, and it is necessary to neutralize such a salt with an alkali such as ammonia in the reaction system. Consequently, a substantial amount of an inorganic salt such as ammonium sulfate is produced inevidably as by-product together with the desired cyclohexanone oxime. Therefore, it has been desired to develop a process for producing a cyclohexanone oxime without producing inorganic salts such as ammonium sulfate, as by-product. Some proposals have been made, but none of them has been fully satisfactory.

For example, Japanese Unexamined Patent Publication No. 125,013/1976 discloses a process for producing an oxime in one step by reacting an aldehyde or a ketone with nitrogen monoxide in the presence of a tin or copper compound and water. This process produces no such an inorganic salt by-product as ammonium sulfate, but the tin or copper compound is required to be used in a large amount of at least equimolar to the resulting oxime, such being economically disadvantageous. Besides, treatment of the metal compound after the reaction is cumbersome.

Under these circumstances, the present inventor has conducted various researches with an aim to develop a novel process for producing an oxime, which does not require use of hydroxylamine sulfate and thus is free from producing ammonium sulfate as by-product. As a result, it has been found that an oxime can be constantly obtained by reacting the corresponding ketone or aldehyde directly with nitrogen monoxide and hydrogen by means of a certain specific catalyst. The present invention has been accomplished on the basis of this discovery.

The present invention provides a process for preparing an oxime, which comprises reacting a ketone or an aldehyde with nitrogen monoxide and hydrogen in the presence of a platinum group metal catalyst to form the corresponding oxime.

Now, the present invention will be described in detail with reference to the preferred embodiments.

In the present invention, a ketone or an aldehyde is directly reacted with nitrogen monoxide and hydrogen. The ketone used in the present invention may be an aliphatic, alycyclic or aromatic compound, such as cyclohexanone, cyclododecanone, acetone, dimethylacetone, acetophenone or benzophenone. The aldehyde may be, for example, acetaldehyde, propionaldehyde, butylaldehyde, caproic aldehyde, benzaldehyde or anisaldehyde. Among these compounds, cyclohexanone is particularly preferred from the practical view point.

In the present invention, it is essential to use a platinum group metal catalyst. The platinum group metal catalyst may usually be a metal such as platinum, palladium, rhodium, ruthenium, osmium or iridium, or an oxide, inorganic acid salt, organic acid salt, sulfide, cyanide or complex salt of such a metal. Among them, platinum metal is preferred. The platinum group metal catalyst is used usually in an amount of from 0.001 to 20 mmol, preferably from 0.05 to 2 mmol, as metal per kg of the reaction solution. If this amount is too small, the oxime as the desired product does not effectively form. On the other hand, if the amount is excessive, no additional effects will be obtained, and such is economically disadvantageous.

The catalyst of the present invention may contain a cocatalyst to further improve the reaction performance. As such a cocatalyst, a metal such as arsenic, antimony, bismuth, mercury, sulfur, selenium or tellulium, or its compounds may be mentioned. Among them, a metal of Group Va, particularly arsenic or antimony, is preferred. The cocatalyst is used usually in an amount of from 0.01 to 1 mol, preferably from 0.1 to 0.4 mol, per mol of the platinum group metal.

The catalyst of the present invention may be the one supported on a carrier. As such a carrier, active carbon, graphite, alumina or silica is usually employed. It is particularly preferred to employ a platinum group metal catalyst supported on active carbon or graphite. In such a case, the platinum group catalyst is supported usually in an amount of from 0.1 to 20% by weight.

The reaction of the present invention is conducted usually by contacting a ketone or an aldehyde in a liquid state with gaseous nitrogen monoxide and hydrogen. This reaction may be conducted in the presence or absence of a solvent for the reaction. The solvent for the reaction used here, is selected taking the nature of the starting material ketone or aldehyde, etc. into consideration. Usually, however, water and/or a water-missible organic solvent such as an aliphatic alcohol e.g. methanol, ethanol or isopropanol, may usually be employed. Further, an organic acid which will be described hereinafter, may be employed also as a solvent. The solvent for the reaction is used usually in an amount of from 0.1 to 100 parts by weight, preferably from 1 to 10 parts by weight, per part by weight of the ketone or the aldehyde. Without using a solvent for the reaction as a third component, an excess amount of the ketone or the aldehyde starting material may be used also as the solvent.

Further, it is preferred to conduct the reaction of the present invention in the presence of a small amount of an acid in the reaction system, whereby the reaction performance is improved, and the desired oxime can be obtained in good yield. As such an acid, an inorganic acid such as sulfuric acid, hydrochloric acid or phosphoric acid, or an organic acid such as acetic acid or formic acid, may be mentioned. The acid is used usually in an amount of from 0.05 to 10% by weight as the acid concentration in the reaction solution, in the case of an inorganic acid. In the case of an organic acid, the amount may be substantial since it may serve also as the solvent. If the acid used here is an inorganic acid, it is necessary to subsequently neutralize it. Accordingly, it is undesirable to use a large amount of an inorganic acid, since formation of a by-product salt will thereby be increased. In the case of an organic acid, it is usually desirable to separate and recover it by e.g. distillation and reuse it.

The reaction of the present invention is considered to proceed as identified by the following reaction schemes.

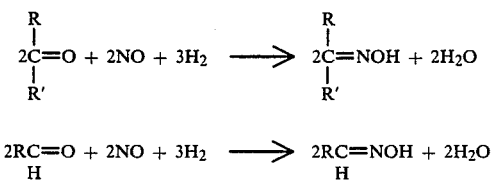

Accordingly, the theoretical amount of nitrogen monoxide is one mol per mol of the ketone or the aldehyde. Likewise, the theoretical amount of hydrogen is 1.5 mols per mol of the ketone or aldehyde. Thus, it is necessary to use such gas components in an amount of at least the respective theoretical amounts. In a case of a gas mixture of nitrogen monoxide and hydrogen, the amount of the hydrogen gas is preferably at least 2 times in volume to the nitrogen monoxide gas in view of the critical limit for explosion.

The reaction temperature in the present invention is usually from 10 to 150° C., preferably from 30 to 80° C. If the temperature is too low, the reaction rate will be slow, whereby it will be difficult to effectively obtain the desired oxime. On the other hand, if the temperature is too high, decomposition of the starting material and the product is likely to result, such being undesirable. The reaction may be conducted under atmospheric pressure or under elevated pressure. The reaction time varies depending upon the type of the starting material, the reaction temperature, etc. and can not generally be defined. However, it is usually from 0.5 to 10 hours.

The practical operation in carrying out the reaction of the present invention comprises, for example, charging into a reactor, the ketone or the aldehyde, the platinum group metal catalyst and, if necessary, a solvent for the reaction composed of water and/or an organic solvent and a small amount of an acid, and introducing gaseous nitrogen monoxide and hydrogen, respectively, to the liquid phase or the gas phase of the reaction system maintained at a predetermined temperature under stirring.

The mixture after the reaction is, if necessary, subjected to filtration to remove the precipitated catalyst, and the acid remaining in the system is neutralized. Then, the formed oxime is isolated and recovered by e.g. distillation.

Now, the present invention will be described in further detail with reference to Examples. However, it should be understood that the present invention is by no means restricted to such specific Examples.

EXAMPLE 1

Into a 1 l glass reactor equipped with a gas supply device, a temperature controlling device and a stirrer, 280 g of cyclohexanone, 600 ml of isopropanol, 100 ml of 30% sulfuric acid and 2 g of a catalyst comprising 2% by weight of platinum and 0.2% by weight of arsenic supported on active carbon, were charged, a gas mixture of $NO/H_2 = \frac{1}{2}$ was supplied to the liquid phase in the reactor at a rate of 700 ml/min under stirring and maintaining the temperature at 50° C., to conduct the reaction for two hours.

After completion of the reaction, aqueous ammonia was added to the mixture to neutralize sulfuric acid. Then, the mixture was subjected to filtration, and the filtrate was analyzed by gas chromatography to confirm formation of the desired cyclohexanone oxime. The yield of the cyclohexanone oxime to the feed NO, was obtained. The results are shown in Table 1. The total amount of the formed cyclohexanone oxime was 2.2 mols, which correspond to about three times in equivalent to the sulfuric acid used.

EXAMPLES 2 and 3

The reaction was conducted in the same manner as in Example 1 except that the reaction time, the reaction solvent and the acid were changed as shown in Table 1. The results are shown in Table 1. Example 2 represents a case where acetic acid serves also as a solvent.

TABLE 1

|  | Reaction time (hr) | Solvent Type | Amount* (times) | Acid Type | Concentration** (wt %) | Yield*** (%) |
|---|---|---|---|---|---|---|
| Example 1 | 2 | Isopropanol | 1.7 | 30% sulfuric acid | 4.4 | 70 |
| Example 2 | 3 | Acetic acid | 2.5 | Acetic acid | 72 | 65 |
| Example 3 | 2 | Isopropanol | 2.0 | Nil | 0 | 35 |

*Amount of the solvent for the reaction: weight ratio to cyclohexanone.
**Concentration of the acid: acid concentration in the liquid phase of the reaction system.
***Yield: yield of cyclohexanone oxime to the feed NO.

EXAMPLE 4

The reaction was conducted in the same manner as in Example 1, except that 0.4 g of platinum black was used as the catalyst, whereby the yield of cyclohexanone oxime was 34%.

EXAMPLE 5

The reaction was conducted in the same manner as in Example 1 except that 2 g of a catalyst comprising 2% by weight of platinum and 0.2% by weight of antimony supported on active carbon was used as the catalyst, whereby the yield of cyclohexanone oxime was 70%.

EXAMPLE 6

The reaction was conducted in the same manner as in Example 5 except that the mixing ratio of $NO/H_2$ was changed to $\frac{1}{4}$ and the flow rate of the gas mixture was changed to 600 ml/min, whereby the yield of cyclohexanone was 65%.

EXAMPLE 7

The reaction was conducted in the same manner as in Example 1 except that instead of cyclohexanone, the same mol amount of acetone was used, and the analysis was conducted in the same manner as in Example 1, whereby formation of the desired acetone oxime was confirmed, and the yield thereof was 68% (relative to the feed NO).

According to the process of the present invention, oximes can be synthesized in one step by using ketones or aldehydes, nitrogen monoxide and hydrogen as starting materials, whereby it is unnecessary to preliminarily prepare hydroxylamine. Thus, the process of the present invention presents an industrially significant merit that a plant for the synthesis of hydroxylamine can be eliminated. Further, in the reaction of the present invention, there is no or little production of an inorganic salt such as ammonium sulfate as by-product. Therefore, the process of the present invention is very advantageous from the economical point of view.

I claim:

1. A process for preparing an oxime, which comprises reacting a ketone or aldehyde selected from the group consisting of cyclohexanone, cyclododecanone, acetone, dimethylacetone, acetophenone, benzophenone, acetaldehyde, propionaldehyde, butylaldehyde, caproic aldehyde, benzaldehyde and anisaldehyde with nitrogen monoxide and hydrogen in the presence of a platinum group metal catalyst selected from the group consisting of platinum, palladium, rhodium, ruthenium, osmium and iridium, and oxides, inorganic acid salts, organic acid salts, sulfides, cyanides and complex salts thereof, at a temperature of 10–150° C., the catalyst being in an amount of 0.001–20 mmol as metal per kg of the reaction solution, the hydrogen being in an amount of at least 1.5 mols per mol of the ketone or aldehyde, and the nitrogen monoxide being in an amount of at least one mol per mol of the ketone or aldehyde.

2. The process according to claim 1, wherein a cocatalyst selected from the group consisting of arsenic, antimony, bismuth, mercury, sulfur, selenium and tellurium is used in an amount of 0.01–1 mol per mol of the platinum group metal.

3. The process according to claim 1, wherein the platinum group metal catalyst is a platinum catalyst.

4. The process according to claim 2, wherein arsenic or antimony is used as the cocatalyst.

5. The process according to claim 1, wherein the platinum group metal catalyst is a catalyst supported on active carbon or graphite.

6. The process according to claim 1 or 5, wherein the catalyst is active carbon having from 0.1 to 20% by weight of platinum supported thereon.

7. The process according to claim 4, wherein the cocatalyst is used in an amount of from 0.1 to 0.4 mol per mol of the platinum group metal.

8. The process according to claim 1, wherein the platinum group metal catalyst is used in an amount of from 0.05 to 2 mmol as metal per kg of the reaction solution.

9. The process according to claim 1, wherein an aliphatic alcohol is used as a solvent for the reaction.

10. The process according to claim 1 or 8 wherein an inorganic acid is present in the reaction system at an acid concentration of from 0.05 to 10% by weight.

11. The process according to claim 1, wherein the hydrogen is used in an amount of at least two times by volume relative to the nitrogen monoxide.

12. The process according to claim 1, wherein the ketone is cyclohexanone.

* * * * *